US008802808B2

(12) United States Patent
Reese et al.

(10) Patent No.: US 8,802,808 B2
(45) Date of Patent: Aug. 12, 2014

(54) CASTING COMPOUNDS BASED ON POLYURETHANE

(75) Inventors: Hans-Juergen Reese, Damme (DE); Ralf Fritz, Bissendorf-Schledehausen (DE); Gunther Lukat, Bohmte (DE); Hans Ulrich Schmidt, Osnabrueck (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 273 days.

(21) Appl. No.: 12/444,397

(22) PCT Filed: Sep. 28, 2007

(86) PCT No.: PCT/EP2007/060326
§ 371 (c)(1),
(2), (4) Date: Apr. 6, 2009

(87) PCT Pub. No.: WO2008/040687
PCT Pub. Date: Apr. 10, 2008

(65) Prior Publication Data
US 2010/0105855 A1   Apr. 29, 2010

(30) Foreign Application Priority Data

Oct. 4, 2006  (EP) ..................................... 06121741

(51) Int. Cl.
| | | |
|---|---|---|
| C08G 18/00 | (2006.01) | |
| C09K 3/00 | (2006.01) | |
| C08G 18/12 | (2006.01) | |
| C08G 18/66 | (2006.01) | |
| B01D 63/02 | (2006.01) | |
| C08G 18/79 | (2006.01) | |
| A61M 1/16 | (2006.01) | |

(52) U.S. Cl.
CPC ............ *C08G 18/6696* (2013.01); *C08G 18/12* (2013.01); *B01D 63/023* (2013.01); *C08G 18/6674* (2013.01); *A61M 1/16* (2013.01); *C08G 18/797* (2013.01)
USPC ........................ 528/76; 252/182.27

(58) Field of Classification Search
CPC .................................. C08G 18/00; C09K 3/00
See application file for complete search history.

(56) References Cited

U.S. PATENT DOCUMENTS

| | | | | |
|---|---|---|---|---|
| 4,293,418 | A | * 10/1981 | Fujii et al. | 210/321.81 |
| 5,306,798 | A | * 4/1994 | Horn et al. | 528/58 |
| 5,451,615 | A | * 9/1995 | Birch | 521/132 |
| 5,885,394 | A | * 3/1999 | Scherzer et al. | 156/242 |
| 6,420,443 | B1 | * 7/2002 | Clark et al. | 521/114 |
| 6,669,407 | B2 | * 12/2003 | Markusch et al. | 405/184.2 |
| 2006/0167125 | A1 | * 7/2006 | Bauer et al. | 521/172 |

FOREIGN PATENT DOCUMENTS

| | | |
|---|---|---|
| DE | 31 49 527 | 6/1983 |
| EP | 0 538 673 | 4/1993 |
| EP | 1 088 841 | 4/2001 |
| EP | 1 090 941 | 4/2001 |
| EP | 1 582 544 | 10/2005 |

OTHER PUBLICATIONS

ITOH Oil Chemical Co. Ltd, Technical Data Sheet. Dec. 15, 2004. all.*
DERWENT English Abstract, EP 1582544 A1, Mar. 2005.*
Abele, L. et al., "Polyurethane, Kunststoff-Handbuch", Hanser, vol. 7, $3^{rd}$ edition, pp. 438-454, (1993).

* cited by examiner

*Primary Examiner* — Randy Gulakowski
*Assistant Examiner* — Jeffrey Washville
(74) *Attorney, Agent, or Firm* — Oblon, Spivak, McClelland, Maier & Neustadt, L.L.P.

(57) ABSTRACT

The invention relates to a polyol mixture which comprises as components
a1) at least one fat-based polyol,
a2) at least one polyetherol having a number average molecular weight of from 500 to 2000 g/mol and
a3) if appropriate one or more crosslinkers having a number average molecular weight of from 90 to 400 g/mol,
where
x) the number average molecular weight of component a1) differs by not more than 400 g/mol from the number average molecular weight of component a2) and
xi) components a1) and a2) do not differ from one another in OH functionality by more than 0.5.
These polyol mixtures can be employed to produce polyurethane-based embedding compositions. The invention additionally relates to embedding compositions based on the polyol mixtures (A) described at the outset and at least one modified isocyanate (B) and to the use of the embedding compositions as potting material. The invention further relates to a process for producing the embedding compositions as described at the outset. The invention additionally relates to dialysis filters which comprise the embedding compositions described at the outset. Finally, the invention relates to the combination of components (A) and (B) which are present separately but are to be used together.

16 Claims, No Drawings

CASTING COMPOUNDS BASED ON POLYURETHANE

The invention relates to a polyol mixture which comprises as components a1) at least one fat-based polyol, a2) at least one polyetherol having a number average molecular weight of from 500 to 2000 g/mol and a3) if appropriate one or more crosslinkers having a number average molecular weight of from 90 to 400 g/mol, where x) the number average molecular weight of component a1) differs by not more than 400 g/mol from the number average molecular weight of component a2) and xi) components a1) and a2) do not differ from one another in OH functionality by more than 0.5.

These polyol mixtures can be employed to produce polyurethane-based embedding compositions. The invention additionally relates to embedding compositions based on the polyol mixtures (A) described at the outset and at least one modified isocyanate (B) and to the use of the embedding compositions as potting material. The invention further relates to a process for producing the embedding compositions as described at the outset. The invention additionally relates to dialysis filters which comprise the embedding compositions described at the outset. Finally, the invention relates to the combination of components (A) and (B) which are present separately but are to be used together.

Preferred embodiments are to be found in the claims and the description. Combinations of preferred embodiments do not depart from the scope of this invention.

Polyurethane (PU)-based embedding compositions are known per se and are comprehensively described for example in the Kunststoff-Handbuch "Polyurethane", volume 7, 3rd edition, 1993, pages 438-454, edited by Dr. G. Oertel, in Carl Hanser Verlag, Munich, Vienna.

The use of polyurethane-based embedding compositions for producing shaped articles for medical technical equipment, especially as potting material for hollow fibers in dialyzers, is likewise known per se and has advantages inter alia because of the simple handling of PU embedding compositions and the small shrinkage thereof during the curing process.

EP-0 538 673 describes transparent, autoclavable, non-cytotoxic polyurethane-based embedding compositions which are obtainable by reacting modified diisocyanates with a polyol component. Suitable constituents disclosed for the polyol component are low molecular weight polyether polyols having an average functionality of from 3 to 8 and a hydroxyl number of from 200 to 1000 mg KOH/g, and either castor oil or polyetherpolyols having a functionality of from 2 to 3 and a hydroxyl number of from 90 to 200 mg KOH/g. Although combinations of both the latter components are not precluded, no statements are made about particularly suitable, especially low-viscosity polyol mixtures.

EP-A-1 090 941 likewise describes transparent, autoclavable, non-cytotoxic polyurethane-based embedding compositions. The polyurethane systems mentioned in this application are based on a modified isocyanate component with specific viscosity and on a polyol component which may comprise inter alia also castor oil mixed with low molecular weight polyetherols having a functionality of from 3 to 8 and a hydroxyl number of from 200 to 1000 mg KOH/g.

DE-31 49 527 A1 describes polyurethane compositions for hollow fiber dialyzers which comprise polyisocyanates and storage-stable polyol mixtures mainly composed of castor oil. The storage-stable polyol mixture normally comprises in addition also compounds which are not compatible with castor oil, have as low a molecular weight as possible and contain hydroxyl groups, e.g. low molecular weight alcohols, and the partial esters thereof with long-chain carboxylic acids as solubilizers.

One disadvantage of the polyol mixtures described in the prior art is the high viscosity after mixing the reactive components. As a consequence thereof, time-efficient embedding in particular of dialysis filters with a large number of fibers is problematic or impossible.

As alternative, EP-A-1 582 544 proposes polyurethane-based embedding systems which have a low viscosity. The proposed compositions are based on use of a particular diol mixture to produce a low-viscosity polyisocyanate prepolymer, preferably employing propylene glycols of varying molecular weight. Polyether alcohols and/or polyester alcohols are proposed as polyol component. The embedding systems proposed in EP-A-1 582 544 are, however, still in need of improvement in relation to the stability during wet sterilization.

One object of the present invention was to provide polyol mixtures which have a low viscosity immediately after mixing with an isocyanate component (called mixed viscosity hereinafter) and thus enable embedding in dialysis filters with a large number of fibers, preferably more than 12 000 fibers per filter. At the same time, it was intended that the embedding compositions produced with the polyol mixtures of the invention show high stability during wet sterilization. One aim was accordingly to provide embedding compositions with only slight uptake of water at high temperatures and high resistance to disinfectants, especially slight desorption of peracetic acid after wet sterilization. It was additionally intended that the embedding compositions show little formation of fine dust on cutting, and a good cuttability over a long period. It was finally intended to achieve favorable adhesion properties between the embedding composition and the casing of medical technical articles. The embedding compositions were additionally intended after curing has taken place in contact with aqueous media to show no desorption of toxic compounds and be transparent.

It has been found that the abovementioned positive properties, especially a low water uptake, a high resistance to disinfectants and good processing properties after curing on the one hand, and a low mixed viscosity on the other hand, can be achieved simultaneously by employing the polyol mixtures of the invention. It has additionally been found that the embedding compositions of the invention have the described excellent properties during wet sterilization and during processing.

A further object finally was to provide a process for producing embedding compositions and dialysis filters, especially those with a large number of fibers, with which a time-efficient embedding even of complex forms is possible without the formation of voids.

Polyol Mixtures

The polyol mixture comprises according to the invention at least one fat-based polyol a1) and at least one polyetherol a2) having a number average molecular weight of from 500 to 2000 g/mol, where the number average molecular weight of the two polyols differs by not more than 400 g/mol and the two polyols do not differ from one another in OH functionality by more than 0.5.

OH functionality means the number of alcoholic, acylatable OH groups per molecule. If the relevant component consists of a compound of defined molecular structure, the functionality emerges from the number of OH groups per molecule. If a compound is prepared by ethoxylation or propoxylation of a starter molecule, the OH functionality emerges from the number of reactive functional groups, for example OH groups, per starter molecule. If mixtures of compounds differing in OH functionality are employed, the OH functionality emerges from the number-weighted average of the OH functionality of the individual compounds.

All molecular weights mentioned in this invention refer to the number average molecular weight. The molecular weight of a mixture or of a component emerges in this connection from the number-weighted molecular weights of the contained compounds. A number average molecular weight is intended to mean hereinafter the value determined by gel permeation chromatography on an Ultrastyragel column system with tetrahydrofuran (THF) as mobile phase and an RI detector at 35° C.

A polyol means a compound which comprises per molecule at least two hydrogen atoms reactive with isocyanate groups. The H atoms reactive with isocyanate groups are preferably derived from hydroxyl groups.

The polyol mixture preferably comprises components a1) and a2) in a ratio of a1) to a2) of from 8:2 to 2:8 by weight. A particularly preferred ratio of components a1) to a2) is from 7:3 to 4:6, for example from 6.5:3.5 to 4.5:5.5, by weight.

If the polyol mixture of the invention comprises a crosslinker a3), the proportion of a3) in the polyols mixture is preferably from 1 to 30% by weight based on the polyol mixture, particularly preferably from 1 to 21% by weight and very particularly preferably from 5 to 10% by weight, in each case based on the polyol mixture.

The polyol mixture preferably comprises the following constituents: from 40 to 70% by weight of component a1), from 30 to 60% by weight of component a2) and from 0 to 30% by weight of component a3), where the total of a1), a2) and a3) is 100% by weight. The polyol mixture particularly preferably comprises the following constituents: from 45 to 65% by weight of component a1), from 34 to 54% by weight of component a2) and from 1 to 21% by weight of component a3), where the total of a1), a2) and a3) is 100% by weight.

The polyol mixture of the invention preferably has a viscosity of up to 1500 mPa·s; a preferred viscosity is up to 1000 mPa·s and a particularly preferred viscosity is up to 700 mPa·s. A very particularly preferred viscosity of the polyol mixture is finally up to 600 mPa·s. It is desired in principle for the viscosity of the polyol mixture to be as low as possible, because a low viscosity leads to a low mixed viscosity in the later production of a polyurethane-based embedding composition. However, a lower limit for the viscosity emerges in practice owing to the composition according to the invention of the polyol mixture. The viscosity of the polyol mixture can be for example in the region of 200 mPa·s or higher, especially in the range from 250 to 600 mPa·s.

The viscosity can be determined for example by means of a rotational viscometer. All the viscosities mentioned in this invention relate to determination as specified in DIN 53018 at a temperature of 25° C. with a rotational viscometer in plate/cone measuring geometry.

Component a1) comprises according to the invention at least one fat-based polyol. Component a1) preferably has an OH functionality of at least 2. Thus, inter alia, mixtures of fat-based polyols each having an OH functionality of at least 2, or mixtures of fat-based polyols resulting in an OH functionality of at least 2 for component a1), are suitable as component a1).

The OH functionality of component a1) is preferably in the range from 2 to 3. Component a1) particularly preferably has an OH functionality of from 2.3 to 3 and very particularly preferably of from 2.6 to 3.

Fat-based polyol is intended to mean a compound based on a fat, an oil, a fatty acid or a fatty acid derivative. A fat-based polyol may be a fat, an oil, a fatty acid or a fatty acid derivative or be obtained from the aforementioned compounds by physical or chemical modification. Fat-based polyols according to the definition mentioned above are known per se to the skilled worker or can be obtained by methods known per se.

Vegetable oils or derivatives thereof are suitable examples of fat-based polyol. Vegetable oils may vary in their composition and occur in various degrees of purity. Vegetable oils complying with the provisions of the German Pharmacopeia (DAB) are preferred in the context of this invention. Component a1) very particularly preferably comprises at least one fat-based polyol which is a vegetable oil complying with DAB-10.

It is additionally possible to use as fat-based polyol generally known fatty acids, preferably natural fatty acids, particularly preferably vegetable fatty acids, in particular unsaturated vegetable fatty acids, and derivatives thereof such as the esters with mono- and/or dialcohols, as long as the properties which are discussed hereinafter in relation to molecular weight and OH functionality are complied with.

However, it is also possible to employ as fat-based polyol for example ring-opened epoxidized or oxidized fatty acid compounds and/or adducts of fatty acid compounds and alkylene oxides. Hydroxylated fatty acids and/or hydroxylated fatty acid derivatives which are obtainable by the aforementioned processes are preferred.

The adducts of OH-functional fat-based compounds, for example castor oil or hydroxylated vegetable oils, and alkylene oxides can be prepared by generally known alkoxylation of the compounds with, for example, ethylene oxide, propylene oxide and/or butylene oxide at temperatures of from 80 to 130° C. and pressures of from 0.1 to 1 MPa, if appropriate in the presence of conventional catalysts such as alkali metal hydroxides or alkali metal alcoholates.

It is also possible to employ as fat-based polyol in addition hydroxylated fatty acid compounds based on rapeseed oil, soybean oil, canola oil, olive oil and/or sunflower oil and/or those based on oleic and/or linoleic acid. Polyols based on hydroxylated soybean oil are particularly suitable as fat-based polyol.

However, a vegetable oil without chemical modification is preferably employed as fat-based polyol. Castor oil is particularly preferred. The especially preferred fat-based polyol is castor oil which complies with the provisions of the German Pharmacopeia DAB 10.

Also preferred are triglycerides of fatty acids having an OH functionality of from 2 to 3. The triglyceride of ricinoleic acid, if appropriate mixed with triglycerides which also comprise further natural fatty acids, for example linoleic acid and/or palmitic acid, are particularly preferred.

Component a1) preferably has a low water content, for example less than 0.2% by weight. A water content of component a1) of less than 0.1% by weight is preferred. If a natural oil, for example castor oil, is employed as component a1), the employment is normally preceded by a purification which may include in particular the removal of suspended matter and dehydration. Natural oils freed of suspended matter and having the abovementioned water content are particularly suitable as component a1).

The polyol can, besides its molecular weight, also be characterized by its hydroxyl number. As is sufficiently well known to the skilled worker, accurate calculation of the hydroxyl number from the molecular weight is possible only when the OH functionality is known. The hydroxyl number of component a1) is preferably from 50 to 350 mg KOH/g, particularly preferably 100 to 300 mg KOH/g, and very particularly preferably 100 to 200 mg KOH/g.

The hydroxyl number of a compound indicates the amount of potassium hydroxide in milligrams which is equivalent to the acetic acid bound by 1 g of the compound on acetylation. The hydroxyl number is a measure of the concentration of hydroxyl groups in a polymer chain. Determination of the hydroxyl number is described in DIN 53240, to which the hydroxyl numbers indicated in this application refer.

Fat-based polyols having a number average molecular weight of from 500 to 2000 g/mol are preferably employed in component a1). Fat-based polyols having a number average molecular weight of from 700 to 1400 g/mol are particularly preferably employed, very particularly preferably of from 800 to 1100 g/mol. Component a1) has a number average molecular weight preferably of from 500 to 200 g/mol, particularly preferably from 700 to 1400 g/mol, and very particularly preferably from 800 to 1100 g/mol.

Particularly preferred as component a1) are fat-based polyols or mixtures of a plurality of fat-based polyols, where the number average molecular weight of component a1) is from 700 to 1400 g/mol and the OH functionality is from 2 to 3; a number average molecular weight of from 800 to 1100 g/mol and an OH functionality of from 2.6 to 3 are very particularly preferred for component a1).

Component a2) comprises according to the invention at least one polyetherol having a number average molecular weight of from 500 to 2000 g/mol. The number average molecular weight of component a2) is preferably in the range from 700 to 1400 g/mol and particularly preferably from 800 to 1100 g/mol.

Component a2) preferably has an OH functionality of from 2 to 4 and particularly preferably of from 2.5 to 3.5. Component a2) very particularly preferably has an OH functionality of 3.

The content of alkali metal ions in component a2) may vary within a wide range as a result of the preparation. The component a2) normally comprises from 0 to 200 ppm alkali metal ions. Component a2) preferably has a low content of alkali metal ions, for example not more than 20 ppm. Component a2) particularly preferably has an alkali metal ion content of not more than 10 ppm.

Polyetherols having the aforementioned properties are known per se to the skilled worker or can be produced by processes known per se, for example by anionic polymerization with alkali metal hydroxides such as sodium or potassium hydroxide or alkali metal alcoholates such as sodium methoxide, sodium or potassium ethoxide or potassium isopropoxide as catalysts and with addition of at least one starter molecule which comprises 2 to 4 reactive hydrogen atoms in bound form, or by cationic polymerization with Lewis acids such as antimony pentachloride, boron fluoride-etherate inter alia or fuller's earth as catalysts from one or more alkylene oxides selected from propylene oxide (PO) and ethylene oxide (EO).

If different alkylene oxides are incorporated into a polyetherol of component a2), these can be used singly, alternately in succession or as mixtures. Use of an EO/PO mixture leads to a polyetherol with random distribution of PO/EO units. It is possible first to employ a PO/EO mixture and then, before termination of the polymerization, to use only PO or EO in order to obtain a polyetherpolyol with a PO or EO end cap.

Examples of suitable starter molecules for preparing the polyetherols of component a2) are: water, organic dicarboxylic acids, diamines such as, for example, optionally mono- and dialkyl-substituted ethylenediamine, diethylenetriamine, triethylenetetramine, 1,3-propylenediamine; and/or 1,3- or 1,4-butylenediamine. Further suitable starter molecules are: alkanolamines such as, for example, ethanolamine, N-methyl- and N-ethylethanolamine, dialkanolamines such as, for example, diethanolamine, N-methyl- and N-ethyldiethanolamine and trialkanolamines such as, for example, triethanolamine and ammonia. It is further possible to employ as starter molecules dihydric, trihydric or tetrahydric alcohols such as ethanediol, propane-1,2- and -1,3-diol, diethylene glycol, dipropylene glycol, butane-1,4-diol, hexane-1,6-diol, glycerol and/or pentaerythritol.

Preferred starter molecules or mixtures of starter molecules are those which lead to polyetherols having the abovementioned preferred OH functionalities.

Component a2) preferably comprises at least one polyetherol based on propoxylated trimethylolpropane or propoxylated glycerol or mixtures of these compounds. Particular preference is given in this connection to propoxylated trimethylolpropane and/or propoxylated glycerol having a number average molecular weight of from 700 to 1400 g/mol, very particularly preferably of from 800 to 1100 g/mol.

Component a2) may in principle comprise one or more of the aforementioned polyetherols. The skilled worker will select mixtures in such a way that the aforementioned properties of component a2) in relation to OH functionality and molecular weight are set up.

According to the invention, the number average molecular weight of component a1) differs by not more than 400 g/mol from the number average molecular weight of component a2), and the OH functionality of component a1) differs from the OH functionality of component a2) by not more than 0.5. The difference in the number average molecular weight is preferably not more than 200 g/mol, very particularly preferably not more than 100 g/mol. The difference in the OH functionalities is preferably not more than 0.4 and very particularly preferably not more than 0.3.

It is particularly preferred for the number average molecular weight of component a1) to differ by not more than 200 g/mol from the number average molecular weight of component a2) and for the OH functionality of component a1) to differ from the OH functionality of component a2) by not more than 0.4. It is very particularly preferred for the number average molecular weight of component a1) to differ from the number average molecular weight of component a2) by not more than 100 g/mol and for the OH functionality of component a1) to differ from the OH functionality of component a2) by not more than 0.3.

Component a3), when present in the polyol mixture, comprises according to the invention one or more compounds which have a crosslinking action and a number average molecular weight of from 90 to 400 g/mol. Crosslinkers a3) preferred in this connection have a molecular weight of from 90 to 300 g/mol, particularly preferably of 150 to 300 g/mol.

The polyol mixtures of the invention may or may not comprise a crosslinker a3). If, however, crosslinkers are employed for example to modify the mechanical properties, it is expedient to employ crosslinkers a3) having an OH functionality of from 3 to 8. Crosslinkers having an OH functionality of from 3 to 4 are preferably employed.

The content of alkali metal ions in the crosslinker a3) is usually as a result of the preparation and may vary within a wide range. Crosslinkers a3) suitable in principle are those with or without alkali metal ions. In one embodiment, the crosslinker a3) has a content of alkali metal ions, preferably potassium ions, of up to 1200 ppm. The content of alkali metal ions, preferably potassium ions, in the crosslinker a3) in this embodiment is preferably up to 1000 ppm and particularly preferably up to 600 ppm. In another embodiment, the crosslinker a) has a low content of alkali metal ions, preferably potassium ions.

Examples of suitable crosslinkers which may be mentioned are: trihydric and higher alcohols such as, for example, glycerol, trimethylolpropane, pentaerythritol, 2,2,6,6-tetrahydroxymethyl-4-oxaheptane-1,7-diol (dipentaerythritol), tripentaerythritol, 3,3,7,7-tetrahydroxymethyl-5-oxanonane (ditrimethylolpropane) and sorbitol and the low molecular weight polyoxypropylene, polyoxyethylene or polyoxypropylene-polyoxyethylene polyols started with these alcohols. The alkoxylated alcohols can be prepared by the processes already mentioned above.

The crosslinkers a3) can also be characterized by their hydroxyl number instead of the molecular weight. As is sufficiently well known to the skilled worker, accurate calculation of the hydroxyl number from the molecular weight is possible only when the OH functionality is known. Crosslinkers a3) with a hydroxyl number of from 400 to 5000 mg KOH/g are preferred, those with a hydroxyl number of from 500 to 5000 mg KOH/g are particularly preferred, and those with a hydroxyl number of 500 to 3000 mg KOH/g are very particularly preferred.

Particularly preferred crosslinkers a3) are those having a molecular weight of from 90 to 300 g/mol and an OH functionality of 3. Polyethylene oxide started with trimethylolpropane and having a molecular weight of form 90 to 300 g/mol is very particularly preferred as crosslinker a3).

It is possible in principle to employ one or more crosslinkers as component a3). The skilled worker will select mixtures of a plurality of crosslinkers in such a way that the number average molecular weight according to the invention and, if appropriate, a preferred OH functionality is achieved.

The polyol mixtures of the invention may, besides components a1), a2) and, if appropriate, a3) mentioned, also comprise further additives. Examples of suitable additives are stabilizers, fillers and/or auxiliaries. The skilled worker will select the additives according to the requirements of the planned use. Stabilizers, fillers and auxiliaries are employed in amounts customary for such additives. For example, the polyol mixtures of the invention when used in embedding compositions for dialysis filters preferably comprise no fillers.

The polyol mixtures of the invention have diverse possible uses. Possible areas of use include synthetic resins and embedding compositions, and plastics, e.g. polyurethanes, including rigid or flexible foams. The polyol mixtures of the invention can additionally be employed as adhesive raw material in adhesive systems and as constituent of paint formulations and coatings. The polyol mixtures are particularly suitable for producing polyurethane-based embedding compositions by reaction with a component which comprises isocyanate groups. Reaction with the modified isocyanates described hereinafter is particularly preferred in this connection. Embedding compositions of the invention can be produced in this way.

Embedding Compositions

An embedding composition within the context of this invention is a mixture of at least two reactive components which is suitable for embedding and which, in liquid or viscous form, is introduced into an article or is applied to an article and subsequently undergoes curing. Such an article may be for example a surface, a vessel with at least one aperture or a mold with at least one recess. The terms embedding composition and casting resin are intended to be understood as equivalent. The properties of the embedding composition: water uptake, peracetic acid desorption, cuttability, wet sterilizability, migration of cytotoxic compounds relate to the cured state.

The embedding compositions comprise according to the invention components based on (A) a polyol mixture of the invention and (B) at least one modified isocyanate based on an isocyanate component b1) and a diol component b2).

The embedding compositions can be obtained by reacting a polyol mixture (A) of the invention with at least one modified isocyanate (B) which can be obtained by reacting an isocyanate component b1) with a diol component b2), if appropriate catalyzed by a catalyst (C).

The ratio between the polyol mixture (A) and component (B) employed can vary within a wide range in this connection. A and B are preferably reacted in amounts such that the equivalence ratio of NCO groups of component B to the total of the reactive hydrogen atoms of component A is from 0.9:1 to 1.3:1, preferably 0.95:1 to 1.2:1 and particularly preferably 1:1 to 1.1:1. The skilled worker will determine the mass ratios to be employed correspondingly.

The embedding compositions of the invention show a low initial mixed viscosity. Mixed viscosity means the viscosity set up immediately after mixing the reactive components. A low mixed viscosity makes it possible to fill molds where a complex structure is present and which require a low viscosity for complete filling. A low viscosity is advantageous for example when embedding dialysis filters with a number of fibers greater than 12 000.

The embedding compositions of the invention normally show a mixed viscosity immediately after mixing the reactive components (A), (B) and, if appropriate, (C) which is up to 1500 mPa·s; a mixed viscosity of up to 1000 mPa·s is preferred, and a mixed viscosity of up to 600 mPa·s is particularly preferred. Finally, a mixed viscosity of up to 500 mPa·s is very particularly preferred. A mixed viscosity which is as low as possible is desired in principle because a low mixed viscosity makes efficient embedding possible. However, on the other hand, technical circumstances result in a practical lower limit for the mixed viscosity. The mixed viscosity can for example be in the region of 200 mPa·s or above, in particular in the range from 250 to 600 mPa·s.

Modified Isocyanate (B)

The modified isocyanate (B) can be obtained according to the invention by reacting an isocyanate component (b1) with a diol component (b2), resulting in polyisocyanate prepolymers. The reaction takes place in a manner known per se by reacting the isocyanate components (b1) described below, for example at temperatures of about 80° C., with diol components (b2) described below, to give a polyisocyanate prepolymer.

It is possible in the context of the invention for the modified isocyanate (B) also to comprise further additives. Additives which can be employed are for example stabilizers, fillers and/or auxiliaries. The skilled worker will employ said additives according to the requirements of the area of application. For example, component B in embedding compositions for dialysis filters preferably comprises no fillers. However, the modified isocyanate (B) normally comprises one or more auxiliaries for controlling the reaction. These auxiliaries influence the reaction of components (b1) and (b2) and/or reduce side reactions in the reaction of (b1) and (b2) and/or during later storage after the reaction has taken place. The modified isocyanate (B) preferably comprises from 0.1 to 10 g of an auxiliary for controlling the reaction per 10 kg of (B). The modified isocyanate (B) particularly preferably comprises from 0.2 to 8 g of an auxiliary for controlling the reaction per 10 kg of (B). Auxiliaries particularly preferably employed for controlling the reaction are diol bischloroformates, in particular diethylene glycol bischloroformate or benzoyl chloride.

Conventional aliphatic, cycloaliphatic and, in particular, aromatic di- and/or polyisocyanates or mixtures thereof are employed as isocyanate component b1). Diisocyanates are particularly suitable, for example tolylene diisocyanate (TDI). Diphenylmethane diisocyanates (referred to as MDI hereinafter) are preferred. If MDI is used it is possible to use all 2-nucleus isomers (2,2'; 2,4' and 4,4'). However, 4,4'-MDI is preferably employed.

The isocyanate component b1) may additionally be in modified form, for example by incorporation of uretdione, carbamate, isocyanurate, carbodiimide, allophanate and urethane groups.

Component b1) preferably comprises from 2 to 10% by weight of a carbodiimide-modified isocyanate. A carbodiimide-modified 4,4'-MDI is particularly preferred in this connection. The isocyanate component b1) very particularly preferably comprises from 3 to 7% by weight of carbodiimide-modified 4,4'-MDI. The stated numerical values in % by weight of carbodiimide-modified isocyanate refer to a carbodiimide-modified isocyanate which comprises 10% by weight of carbodiimide. If the carbodiimide content differs, the skilled worker will recalculate the stated values appropriately.

Organic polyhydroxy compounds having an OH functionality of from 1.5 to 2.5 are employed as diol component b2). The OH functionality is preferably in the range from 1.8 to 2.2, and a diol compound having an OH functionality of 2 is particularly preferably employed. Alkoxylated diol compounds in particular are preferred as diol component b2). Propylene glycols are particularly preferred as diol component b2).

Suitable propylene glycols include (mono)propylene glycol and dipropylene glycol, and oligo- and polypropylene glycols, it being possible to prepare the latter starting from a diol compound by propoxylation.

Diol component b2) comprises according to the invention a mixture of at least two different propylene glycols differing in number average molecular weight.

The diol component b2) preferably comprises at least two different propylene glycols b2x) and b2y) as constituents differing in molecular weight, employing as constituent b2x) a propylene glycol having a molecular weight of from 700 to 1300 g/mol and as constituent b2y) a propylene glycol having a molecular weight of from 50 to 200 g/mol.

The diol component (b2) particularly preferably comprises a mixture comprising at least three different propylene glycols b2x), b2y) and b2z) as constituents differing in molecular weight, employing as constituent b2x) a propylene glycol having a number average molecular weight of from 700 to 1300 g/mol, as constituent b2y) a propylene glycol having a number average molecular weight of from 250 to 650 g/mol and as constituent b2z) a propylene glycol having a number average molecular weight of from 50 to 200 g/mol. Dipropylene glycol is particularly preferred as constituent b2z).

If the diol component b2) comprises two different propylene glycols b2x) and b2y) differing in molecular weight, the two constituents b2x) and b2y) are preferably employed in a mixing ratio of from 40 to 60% by weight of b2x) and from 60 to 40% by weight of b2y). From 45 to 55% by weight of b2x) and from 55 to 45% by weight of b2y) are particularly preferably employed, the total of b2x) and b2y) being 100% by weight in each case.

If the diol component b2) comprises at least 3 different propylene glycols having the properties mentioned under b2x), b2y) and b2z), then the three components b2x), b2y) and b2z) are preferably employed in the following ratio: from 30 to 40% by weight of b2x), from 30 to 40% by weight of b2y) and from 20 to 40% by weight of b2z). From 32 to 36% by weight of b2x), from 35 to 39% by weight of b2y) and from 25 to 33% by weight of b2z) is particularly preferably employed, the total of b2x), b2y) and b2z) being 100% by weight in each case.

The modified isocyanate (B) preferably has an NCO content of from 18 to 28% by weight, particularly preferably from 20 to 25% by weight.

The modified isocyanate (B) additionally has a viscosity of from 250 to 1500 mPa·s; a viscosity of from 250 to 1000 mPa·s is preferred, and a viscosity of from 250 to 500 mPa·s is particularly preferred.

The described modified isocyanates show high storage stability and no unwanted crystallization even at low temperatures.

Catalyst C

The embedding compositions of the invention can be prepared in the absence or in the presence of catalysts. However, the embedding compositions are preferably prepared in the presence of catalysts which greatly speed up the reaction of the modified isocyanate (B) with the polyol mixture (A).

Suitable catalysts (C) are organic metal compounds, preferably organic tin compounds, in particular the tin(II) salts of organic carboxylic acids, such as tin(II) diacetate, tin(II) dioctoate, tin(II) diethylhexoate and tin(II) dilaurate, and the dialkyltin(IV) salts of organic carboxylic acids, such as, for example, dibutyltin(IV) diacetate, dibutyltin(IV) dilaurate, dibutyltin(IV) maleate and dioctyltin(IV) diacetate. Catalysts of this type are described for example in DE-A-3 048 529.

Dialkyltin(IV) mercapto compounds have proved particularly well suited, such as bislauryltin(IV) dimercaptide, and compounds of the general formulae $R_2Sn(SR'-O-CO-R'')_2$ or $R_2Sn(SR'-CO-OR'')_2$ in which R is an alkyl radical having at least 8 carbon atoms, R' is an alkylene radical having at least two carbon atoms and R'' is an alkyl radical having at least four carbon atoms. Examples of catalysts of this type, which are described for example in DD-A-218 668, and which may be mentioned are: dioctyltin(IV) bis(thioethylene glycol 2-ethylhexoate), dioctyltin(IV) bis(thioethylene glycol laurate), dioctyltin(IV) bis(2-ethylhexyl thiolatoacetate, dioctyltin(IV) bis(hexyl thiolatoacetate) and dioctyltin (IV) bis(lauryl thiolatoacetate).

Catalysts which have proved very suitable are also organotin compounds having tin-oxygen or tin-sulfur bonds like those described for example in DD-A-255 535 and corresponding to the general formulae $(R_3Sn)_2O$, $R_2SnS$, $(R_3Sn)_2S$, $R_2Sn(SR')_2$ or $RSn(SR')_3$, where R and R' are alkyl groups comprising 4 to 8 carbon atoms in R and 4 to 12 carbon atoms in R', and R' may additionally be —R''COOR''' and —R''OCOR''' in which R'' are alkyl groups having 1 to 6 carbon atoms and R''' are alkylene groups having 4 to 12 carbon atoms. Examples thereof which may be mentioned are: bis(tributyltin) oxide, dibutyltin(IV) sulfide, dioctyltin (IV) sulfide, bis(tributyltin) sulfide, dibutyltin(IV) bis(2-ethylhexyl thioglycolate), dioctyltin(IV) bis(2-ethylhexyl thioglycolate), octyltin(IV) tris(2-ethylhexyl thioglycolate), dioctyltin(IV) bis(thioethylene glycol 2-ethylhexoate) and dibutyltin(IV) bis(thioethylene glycol laurate). Catalysts preferably used are mono-n-octyltin (2-ethylhexyl thioglycolate) and di-n-octyltin bis(2-ethylhexyl thioglycolate). Catalysts (C) based on dioctyltin (IV) dimercaptide are particularly preferred.

The catalysts (C) can be employed singly or in the form of catalyst combinations.

The present invention comprises both the embedding compositions which can be prepared from the described components, and the combination of the components of (A) a polyol mixture of the invention and (B) a modified isocyanate described above, which are present separately but are to be used together.

If catalysts are employed for preparing the embedding compositions of the invention, these are preferably mixed with the polyol mixture (A) which is finally mixed and reacted with component (B).

The catalysts are normally employed in an amount of from 0.001 to 0.2 parts by weight, preferably from 0.005 to 0.015 parts by weight per 100 parts by weight of the polyol mixture (A).

The process for preparing the embedding compositions of the invention comprises according to the invention the mixing of a polyol mixture (A) of the invention, if appropriate comprising a catalyst (C), with at least one modified isocyanate (B).

The mixing preferably takes place in this case by using a polyurethane two-component processing machine. The mixed viscosity set up immediately after mixing has taken place in the process of the invention is preferably in the range defined hereinbefore. The embedding compositions are then used for embedding and subjected to curing.

Embedding is intended to mean every measure which confers on the initially pourable embedding composition the form which it has after curing. Embedding is intended in particular to mean the introduction into or the application onto an article. Such an article may be for example a surface, a frame, a vessel having at least one aperture or a mold having at least one recess. The embedding composition can in principle remain in contact with the article or be dissolved out of the latter. The embedding composition is preferably not, after curing has taken place, separated from the mold but forms a unit with the latter.

The advantages of the process are evident in particular or embedding in a complex mold which comprises a plurality of corners and/or edges which are to be enveloped by the embedding composition.

The curing can in principle take place in one or more steps which differ in the surrounding conditions, especially the temperature. For example, the curing can take place in a precuring step and in an after-curing step. However, curing in one step is preferred.

The curing generally takes place without further assistance through reaction of the NCO groups with the reactive hydrogen atoms, in particular of the OH groups. The temperature and the atmosphere of the surroundings during the curing step is monitored and/or controlled if appropriate. A chemical crosslinking reaction generally takes place during the curing. The curing is complete as soon as the embedding composition has substantially attained its final properties, in particular its final hardness.

The curing normally takes place in a period from minutes up to several hours, for example from 0.3 to 4 hours, preferably in a period from 1 to 3 hours.

The embedding compositions of the invention generally show after curing has taken place a hardness on the Shore D scale of from 50 to 70. However, the embedding compositions of the invention show a hardness on the Shore D scale of from 55 to 65. A hardness on the Shore D scale of from 58 to 62 is particularly preferred for example for applications as embedding composition in dialysis filters. The hardness on the Shore D scale refers to DIN 53505 at a temperature of 23° C.

The skilled worker will select the composition of the embedding compositions, for example the nature and amount of the crosslinker a3) accordingly.

Depending on the area of application, the embedding compositions may be ready for use only after a purification step, for example a sterilization step in the case of embedding compositions in dialysis filters.

The embedding compositions of the invention have diverse possible uses. The possible applications include the use as molding composition, for example in mold construction or in the production of prototypes, and as potting material, e.g. as embedding composition for components in the electrical and electronics sectors or in medical devices. The use as potting material is preferred. The embedding compositions of the invention are employed in particular as potting material in the electrical or electronics sector and in the filtration of aqueous media. Medical technical applications are particularly preferred. The use of the embedding compositions for embedding hollow fibers, especially in dialysis filters, is very particularly preferred.

Dialysis Filters

A so-called dialysis filter or dialyzer is the component in a dialysis machine which comprises the exchange membrane on which the mass transfer takes place during the detoxification of blood. So-called capillary dialyzers are predominantly employed, and the dialysis filters mentioned in the present invention relate thereto. The dialysis filters consist of a bundle of hollow fibers which normally comprises from 10 000 to 15 000 fibers, and which is embedded in each case at two ends of a hollow article in a matrix of an embedding composition. The hollow article normally consists of a transparent plastic, for example polycarbonate, and is incorporated into a dialyzer housing in such a way that blood can be passed through the interior of the hollow fibers. The dialysis fluid flows round the hollow fibers through which blood flows in the hollow article of the dialysis filter. The wall of the hollow fibers forms the actual filter membrane on which mass transfer takes place during the dialysis treatment.

The process for producing the dialysis filters of the invention comprises according to the invention the mixing of a polyol mixture (A) of the invention, if appropriate comprising a catalyst (C), with a modified isocyanate (B).

The mixing of the described components preferably takes place using a polyurethane two-component processing machine. The mixed viscosity which is set up immediately after mixing has taken place is, in the process of the invention, preferably in the range from 250 to 600 mPa·s; it is particularly preferably in the range from 300 to 500 mPa·s. The reaction mixture is then introduced in a metered amount into the mold comprising hollow fibers.

Introduction of the embedding composition in this case preferably takes place in a hollow article rotating in a centrifuge and comprising hollow fibers, the hollow article being a preliminary stage of a dialysis filter. The liquid reaction mixture is conveyed by centrifugal force to the respective two ends of the dialysis filter to envelop the hollow fibers and undergoes curing to the compact, substantially clear embedding.

The curing step in turn takes place without further assistance by reaction of the NCO groups with reactive hydrogen atoms, in particular of the OH groups. The curing step is complete as soon as the embedding composition has substantially reached its final properties, in particular its hardness and its stability during wet sterilization and the absence of migration of cytotoxic compounds.

The apertures of the hollow fibers are normally exposed by a subsequent cutting process. The dialysis filter is generally ready for use after a purifying and sterilizing process.

It is possible by the process of the invention to produce embedding compositions which are autoclavable and not cytotoxic and thus can be employed in the medical technical sector and which simultaneously completely envelop complex structures, for example a large number of fibers in a dialysis filter.

The cured embedding compositions are resistant to disinfectants. In particular, the embedding compositions of the invention show a small uptake of water vapor or boiling hot water. The embedding compositions of the invention can be cut over a period of two weeks without the formation of fine dust which may otherwise block the pores. The cured embedding compositions of the invention are transparent, not cytotoxic and have an improved adhesion to other materials, e.g. polycarbonates, at elevated temperatures over a prolonged period. The embedding compositions are stable toward percarboxylic acids, so that shaped articles made of such embedding compositions can be sterilized with peracetic acid. The embedding compositions of the invention show high hydrophobicity and adequate crosslinking density.

The still pourable embedding compositions can be used for embedding also without foaming. At the same time, the embedding compositions show a low mixed viscosity immediately after mixing the reactive components. The embedding compositions can be cut after only two hours, but do not harden much subsequently, so that they can still be cut even after more than 24 hours. A further advantage is that the polyurethane-based embedding compositions of the invention can be processed with all usual types of hollow fibers, such as, for example, cuprophane, polysulfone, polycarbonate or cellulose fibers, and the polycarbonates require no pretreatment by corona discharge to improve the adhesion before processing.

The polyol mixtures of the invention thus lead in combination with suitable modified isocyanates to embedding compositions having the aforementioned advantages and make it possible, through the low resulting mixed viscosity, for complex structures to be embedded time-efficiently.

EXAMPLES

1. Determination of the Characteristic Values

The viscosity was determined as specified in DIN 53018 at a temperature of 25° C. with a Haake rotational viscometer (plate/cone measuring unit). The mixed viscosity was determined by calculation since it relates to time zero, i.e. immediately before the start of the reaction. The following formula was used: log(mixed viscosity)={mass fraction of component (A)*log(viscosity (A))+mass fraction of component (B)*log (viscosity (B))}, where the total of the mass fractions of component (A) and (B) is one.

The water uptake was determined by boiling previously weighed round test specimens with a diameter of 68 mm and a thickness of 5 mm in a vessel with water for 5 hours. The mass was then redetermined and the percentage increase in weight was ascertained.

The peracetic acid desorption was determined by storing 5 g of the embedding composition in the form of several circular test pieces with a thickness of 1 mm and a diameter of 35 mm in 100 ml of an aqueous solution which comprises 3.5% by weight of peracetic acid and 26% by weight of hydrogen peroxide at 20° C. for 2 hours. The test piece was then rinsed once with distilled water and stored in 100 ml of distilled water with regular stirring. After storage for four hours, the amount of peroxo compound dissolved out was determined by iodometry by back-titration of oxidized iodide with a 0.01 molar thiosulfate solution.

The OH functionality was determined by calculation according to the formula hydroxyl number [in mg/g KOH]* number average molecular weight/56100=OH functionality.

The Shore D hardness was determined as specified in DIN 53505 (temperature 23° C.).

2. Starting Materials

TABLE 1

| Polyol mixture (A) | | |
|---|---|---|
| Fat-based polyol a1) | a1-1) | Castor oil complying with DAB-10 |
| Polyetherol a2) | a2-1) | Trimethylol-started polyoxypropylene MW = 1040 g/mol |
| | a2-V2) | Polyether polyol based on sucrose/ pentanediol/diethylene glycol/ polyoxypropylene with MW = 450 g/mol and OH— functionality 4 |
| | a2-V3) | Glycerol-started polyether polyol based on ethylene oxide and propylene oxide MW = 3550 g/mol and OH functionality 2.6 |
| Crosslinker a3) | a3-1) | Trimethylol-started polyoxyethylene MW = 180 g/mol |
| | a3-2) | Trimethylol-started polyoxypropylene MW = 200 g/mol |
| Catalyst C) | | Dioctyltin(IV) dimercaptide |

MW = molecular weight

TABLE 2

| Modified isocyanate (B) | | |
|---|---|---|
| Isocyanate component b1) | b1-1) | 4,4'-MDI |
| | b1-2) | Carbodiimide-modified 4,4'-MDI with a carbodiimide content of 10% by weight |
| Diol component b2) | b2-1) | Propylene glycol with MW = 1080 g/mol |
| | b2-2) | Propylene glycol with MW = 450 g/mol |
| | b2-3) | Dipropylene glycol |

MW = molecular weight

3. Preparation of the Components

Polyol Mixture 10 kg of the polyol mixture (A) were prepared in each case from a1), a2), a3) and (C) by mixing the components and weight ratios indicated in Tables 1 and 3 with stirring at room temperature.

Modified Isocyanate

Component b1-1) was introduced into a stirred laboratory reactor with heating and cooling device. Component b1-2) was added if appropriate, and the two isocyanates were mixed. A mixture was prepared from components b2-1), b2-2) and b2-3), and 0.7 g of diglycol bischloroformate was added per 10 kg of modified isocyanate. The glycol mixture in this case was slowly added with stirring to the isocyanate, and the onsetting reaction of the NCO groups with the reactive hydrogen atoms was controlled so that conversion of the glycol mixture with the isocyanate present in excess took place at 80° C. over a period of 60 min, followed by a cooling phase.

4. Production of the Embedding Compositions and Dialysis Filters

The described components were mixed in the mixing ratio indicated in Table 4 using a polyurethane two-component processing machine, and the reaction mixture was introduced in the accurately metered amount into the rotating dialysis filter packed with hollow fibers.

5. Compositions

TABLE 3

Composition of the polyol mixtures

| Example | Polyol a1) a1-1) | Polyetherol a2) a2-1) | a2-V2) | a2-V3) | Crosslinker a3) a3-1) | a3-2) |
|---|---|---|---|---|---|---|
| | Proportion in % by weight in (A) | | | | | |
| 1 | 56.4 | 37.6 | 0 | 0 | 6 | 0 |
| 2V | 94 | 0 | 0 | 0 | 6 | 0 |
| 3V | 0 | 75 | 25 | 0 | 0 | 0 |
| 4V | 79 | 0 | 21 | 0 | 0 | 0 |
| 5V | 43 | 0 | 0 | 43 | 0 | 14 |

TABLE 4

Composition of the embedding compositions

| Example | Polyol mixture (A) according to Example | Catalyst (C) Addition in g per kg of (A) | Mass ratio A:B | Isocyanate component b1) b1-1) | b1-2) | Diol component b2) b2-1) | b2-2) | b2-3) |
|---|---|---|---|---|---|---|---|---|
| | | | | Proportion % by weight in (B) | | | | |
| 6 | 1 | 0.6 | 100:72 | 79 | 4 | 5.8 | 6.3 | 4.9 |
| 7V | 2V | 0.6 | 100:70 | 87 | 0 | 0 | 4.9 | 8.1 |
| 8V | 3V | 0.8 | 100:86 | 67.5 | 4 | 20 | 8.5 | 0 |
| 9V | 4V | 0.8 | 100:72 | 87 | 0 | 0 | 4.9 | 8.1 |
| 10V | 5V | 0.8 | 100:72 | 87 | 0 | 0 | 4.9 | 8.1 |

TABLE 5

Comparison of the properties of the embedding compositions

| Example | Viscosity of (A) | Viscosity of (B) [mPa·s] | Mixed viscosity | Water uptake [% by weight] | Hardness [Shore D scale] | Peracetic acid desorption [ppm] |
|---|---|---|---|---|---|---|
| 6 | 535 | 360 | 454 | +0.97 | 61 | 69.5 |
| 7V | 820 | 650 | 745 | +0.77 | 60 | 29.8 |
| 8V | 450 | 350 | 400 | +1.96 | 60 | 268.1 |
| 9V | 787 | 650 | 727 | +0.81 | 72 | n.d. |
| 10V | 863 | 650 | 767 | +1.82 | 58 | n.d. | n.d.: determined

We claim:

1. A dialysis filter adapted for mass transfer that takes place during the detoxification of blood comprising an embedding composition which comprises components based on
   (A) a polyol mixture and
   (B) at least one modified isocyanate based on an isocyanate component b1) and a diol component b2),
   wherein the polyol mixture comprises as components
   a1) at least one fat-based polyol,
   a2) at least one polyetherol having a number average molecular weight of from 500 to 2000 g/mol and
   a3) one or more crosslinkers having a number average molecular weight of from 90 to 400 g/mol,
   wherein
   the number average molecular weight of component a1) differs by not more than 400 g/mol from the number average molecular weight of component a2) and
   components a1) and a2) do not differ from one another in OH functionality by more than 0.5,
   the polyol mixture, based on the total weight of a1), a2) and a3), comprises from 45 to 65% by weight of component a1), from 34 to 54% by weight of component a2) and from 1 to 21% by weight of component a3), and
   the diol component b2) is a mixture of at least two different propylene glycols differing in number average molecular weight.

2. The dialysis filter according to claim 1, wherein component a1) comprises at least one polyol based on castor oil.

3. The dialysis filter according to claim 1, wherein components a1) and a2) each have an OH functionality of from 2.6 to 3.

4. The dialysis filter according to claim 1, wherein said polyetherol component a2) comprises a compound from the group consisting of propoxylated trimethylolpropane and propoxylated glycerol.

5. The dialysis filter according to claim 1, wherein the diol component b2) is a mixture which comprises at least three different propylene glycols differing in molecular weight, where at least one of the propylene glycols has a number average molecular weight of from 700 to 1300 g/mol, at least one of the propylene glycols has a number average molecular weight of from 250 to 650 g/mol and at least one of the propylene glycols has a number average molecular weight of from 50 to 200 g/mol.

6. The dialysis filter according to claim 1, wherein the number average molecular weight of component a1) differs by not more than 200 g/mol from the number average molecular weight of component a2).

7. The dialysis filter according to claim 1, wherein the number average molecular weight of component a1) differs by not more than 100 g/mol from the number average molecular weight of component a2).

8. The dialysis filter according to claim 1, wherein components a1) and a2) do not differ from one another in OH functionality by more than 0.4.

9. The dialysis filter according to claim 1, wherein components a1) and a2) do not differ from one another in OH functionality by more than 0.3.

10. The dialysis filter according to claim 1, wherein component a2) has a number average molecular weight of from 700 to 1400 g/mol.

11. The dialysis filter according to claim 1, wherein component a2) has a number average molecular weight of from 800 to 1100 g/mol.

12. The dialysis filter according to claim 1, wherein component a1) comprises a polyol based on castor oil and component a2) comprises a propoxylated glycerol.

13. The dialysis filter according to claim 1, which comprises at least 10,000 hollow fibers.

14. A dialysis filter adapted for mass transfer that takes place during the detoxification of blood comprising an embedding composition produced by a process comprising mixing of (A) a polyol mixture and, optionally, a catalyst (C), with
(B) at least one modified isocyanate based on an isocyanate component b1) and a diol component b2)

wherein the polyol mixture comprises as components a1) at least one fat-based polyol,
a2) at least one polyetherol having a number average molecular weight of from 500 to 2000 g/mol and
a3) one or more crosslinkers having a number average molecular weight of from 90 to 400 g/mol, wherein the number average molecular weight of component a1) differs by not more than 400 g/mol from the number average molecular weight of component a2) and components a1) and a2) do not differ from one another in OH functionality by more than 0.5, the polyol mixture, based on the total weight of a1), a2) and a3), comprises from 45 to 65% by weight of component a1), from 34 to 54% by weight of component a2) and from 1 to 21% by weight of component a3), and the diol component b2) is a mixture of at least two different propylene glycols differing in number average molecular weight.

15. The dialysis filter according to claim 14, wherein a viscosity for the mixture of up to 600 mPa·s is established.

16. The dialysis filter according to claim 14, which comprises at least 10,000 hollow fibers.

* * * * *